United States Patent [19]

Lindahl et al.

[11] Patent Number: 4,629,620
[45] Date of Patent: Dec. 16, 1986

[54] MEMBRANE-COATED SUSTAINED-RELEASE TABLETS AND METHOD

[75] Inventors: Ake R. Lindahl, Skurup; Stig A. B. Erlandsson, Malmo, both of Sweden

[73] Assignee: AB Ferrosan, Malmo, Sweden

[21] Appl. No.: 777,957

[22] Filed: Sep. 19, 1985

Related U.S. Application Data

[63] Continuation of Ser. No. 647,928, Sep. 5, 1984, Pat. No. 4,557,925, which is a continuation of Ser. No. 396,391, Jul. 8, 1982, abandoned.

[51] Int. Cl.$^4$ ............... A61K 9/28; A61K 9/32
[52] U.S. Cl. ........................... 424/15; 424/16; 424/19; 424/21; 424/22; 424/32; 424/33
[58] Field of Search ............ 424/15, 16, 19-22, 424/32, 33; 427/2, 3

[56] References Cited

U.S. PATENT DOCUMENTS

| | | | |
|---|---|---|---|
| 3,247,066 | 4/1966 | Milosovich | 424/20 |
| 3,275,518 | 9/1966 | Endicott et al. | 424/33 |
| 3,453,360 | 7/1969 | Hill | 424/33 |
| 3,538,214 | 11/1970 | Polli et al. | 424/33 |
| 3,835,221 | 9/1974 | Fulberth et al. | 424/33 |
| 3,923,939 | 12/1975 | Baker et al. | 424/21 |
| 3,954,959 | 5/1976 | Pedersen | 424/20 |
| 3,965,255 | 6/1976 | Bloch et al. | 424/33 |
| 4,083,949 | 4/1978 | Benedikt | 424/20 |
| 4,177,256 | 12/1979 | Michaels et al. | 424/20 |
| 4,193,985 | 3/1980 | Bechgaard et al. | 424/33 |
| 4,218,433 | 8/1980 | Kooichi et al. | 424/33 |
| 4,244,941 | 1/1981 | Lerk | 424/33 |
| 4,557,925 | 12/1985 | Lindahl et al. | 424/19 |

OTHER PUBLICATIONS

Bonnet, C.A. 83, #180527x (1975).
Rice, C.A. 71, #103242a (1969).
Drinberg, C.A. 77, #128188z (1972).
Ando, C.A. 87, #76494 (1977).
Kimoto, C.A. 89, #25668z (1978).
Kawasaki, C.A. 89, #25678o (1978).
Taguchi, C.A. 80, #146770z (1974).
Comstock, C.A. 71, #51335m (1969).
Kallstrand and Ekman, Journal of Pharmaceutical Sciences 72, No. 7, (Jul. 1983), pp. 772-775.
"Research Disclosure", vol. 135, (Jul. 1975), item 13577 entitled Process for Making Microporous Membranes.
Antelfinger, C.A. 71, #14276x (1969).

Primary Examiner—Shep K. Rose
Attorney, Agent, or Firm—Gordon W. Hueschen

[57] ABSTRACT

A sustained-release coated pharmaceutical tablet comprising a drug-containing tablet and a coating or membrane surrounding the same, wherein the coating or membrane is water-insoluble and insoluble in gastrointestinal fluids and consists essentially of a terpolymer of polyvinylchloride, polyvinylacetate, and polyvinylalcohol and a water-soluble pore-creating substance, the said pore-creating substance being randomly distributed in said terpolymer coating, said pore-creating substance being present in amount of one part to 35 parts for each one to ten parts of terpolymer, said coated tablet exhibiting a substantially constant dissolution rate during a major portion of its dissolution time when exposed to gastrointestinal fluids, especially wherein the terpolymer contains 80 to 95% weight per weight of polyvinylchloride, 0.5 to 19% weight per weight of polyvinylacetate, and 0.5 to 10% weight of polyvinylalcohol, and a method for the preparation thereof, are disclosed.

17 Claims, 7 Drawing Figures

Fig. 1.

MEMBRANE-COATED POTASSIUM CHLORIDE

Fig. 3.

ENTERIC-COATED SODIUM SALICYLATE (A) vs
MEMBRANE-COATED SODIUM SALICYLATE (B)

MEMBRANE-COATED SUSTAINED-RELEASE TABLETS AND METHOD

This is a continuation of U.S. application Ser. No. 647,928, filed Sept. 5, 1984, now U.S. Pat. No. 4,557,925, issued Dec. 10, 1985, which is in turn a continuation of U.S. application Ser. No. 396,391, filed July 8, 1982, now abandoned.

BACKGROUND OF THE INVENTION

1. Field of the Invention

Membrane-coated sustained-release tablets, such membrane-coated tablets having a water-soluble pore-creating substance distributed in the membrane coating.

2. Prior Art

The prior art is replete with innumerable sustained-release pharmaceutical compositions, including membrane-coated sustained-release tablets, which have had greater or lesser degrees of success and which accomplish the desired result, namely, the attainment of a substantially constant and sustained dissolution rate during a major portion of their dissolution time when exposed to gastrointestinal fluids, to a greater or lesser extent. Some of the prior-art membrane-coated sustained-release tablets comprised a water-soluble pore-creating substance in the membrane coating for the creation of pores therein to assist with the entering of gastrointestinal fluids into the membrane for dissolution of the tablet therewithin and subsequent emission of the dissolved tablet, including the drug or medicament therein, in solution form into the system. Representative of prior art attempts to provide a superior membrane-coating and membrane-coated sustained-release pharmaceutical tablet include Hotko, et al. U.S. Pat. No. 3,325,365, issued June 13, 1967, covering an enteric tablet having compressed onto the core a solid granulate composition comprising the physiological active material and the enteric coating. Mention may also be made of Groppenbacher, et al., U.S. Pat. No. 4,060,598 and U.S. Pat. No. 3,935,326, Polli, et al., U.S. Pat. No. 3,538,214 of Merck issued Nov. 3, 1979, as well as Daum, et al., U.S. Pat. No. 3,420,931, and British Patent No. 1,186,990 of Ercopharm A/S. These patents in general approach the problem of membrane-coated sustained-release compositions, including tablets, from the standpoint of employing a pore-creating substance in one way or another, employing different types of insoluble polymers as the membrane-coating, varying the number of coats, varying the pore-creating substance, et cetera ad infinitum, but with less than satisfactory results. This is evidenced by the constantly increasing efforts to modify the approach and the technology for purposes of improving the result, but almost always with a concomitant increase in complexity of the product, the technique, and of course with increased cost. Accordingly, there exists a clear and ever-increasing demand for a simple but still highly effective and superior sustained-release tablet which will exhibit a substantially constant dissolution rate over an extended period of time and during a major portion of its dissolution time when exposed to gastrointestinal fluids of the subject to whom or to which administered, and the fulfillment of this demand is one of the objects of the present invention, as will become more fully apparent hereinafter. This object of the invention is accomplished by the provision of the novel membrane-coated sustained-release tablets of the present invention and the method of producing the same and is possible due to the discovery of unique and valuable characteristics of a particular terpolymer which is used as the water-insoluble and gastrointestinal fluid-insoluble membrane coating for the sustained-release tablets of the invention and which, together with the pore-creating substance randomly distributed therethrough, imparts highly desirable and superior characteristics of dissolution rate and, accordingly, also blood levels, to the particular membrane-coated sustained-release pharmaceutical tablets of the present invention.

A further disadvantage of the membranes or coatings of the prior art has been their inadequate adhesion characteristics with respect to tablets having both high and low energy surfaces, and this shortcoming is likewise overcome by provision of the method and product of the invention, according to which the membrane coating adheres tenaciously to both high and low energy tablet surfaces.

The employment of the terpolymers of the present invention as the membrane-coating for sustained-release tablets, and the extremely valuable characteristics thereof when combined with the water-soluble pore-creating substance, have not previously been suggested in the prior art, nor has it been suggested that the excellent adhesion, dissolution rates, and blood levels could be attainable with any membrane-coated sustained-release tablet wherein such terpolymers are employed as the water-insoluble and gastrointestinal fluid-insoluble membrane coating. This is although the terpolymers of the present invention are known materials from U.S. Pat. Nos. 3,595,939, 3,444,122, and 2,852,499, Federal Republic of Germany Patent No. 1 087 353 of Aug. 18, 1960, British Patent Specification No. 862 978 published Mar. 15, 1961, and British Patent Specification No. 883 070 published Nov. 22, 1961, or from one of the following Chemical Abstracts references: CA 71, 103242a, CA 71, 14276x (1969), and CA 83, 180527x (1975).

OBJECTS

It is an object of the present invention to provide a novel membrane-coated sustained-release pharmaceutical tablet and a method of producing the same.

Another object of the invention is the provision of such a membrane-coated sustained-release pharmaceutical tablet wherein the coating or membrane is water-insoluble and insoluble in gastrointestinal fluids and consists essentially of a terpolymer of polyvinylchloride, polyvinylacetate, and polyvinylalcohol and a water-soluble pore-creating substance, the pore-creating substance being present in amount of one part to 35 parts for each one part to ten parts of terpolymer, the said coated tablet exhibiting a substantially constant dissolution rate during a major portion of its dissolution time when exposed to gastrointestinal fluids.

A further object of the invention is the provision of such a coated tablet wherein the terpolymer contains about 80 to 95% weight per weight of polyvinylchloride, 0.5 to 19% weight per weight of polyvinylacetate, and 0.5 to 10% weight per weight of polyvinylalcohol.

Still another object of the invention is the provision of such a membrane-coated sustained-release pharmaceutical tablet wherein the terpolymer constituting the membrane-coating has the approximate molecular formula (PVC)M; (PVAC)N; (PVOH)O, wherein the PVC is polyvinylchloride, PVAC is polyvinylacetate, and PVOH is polyvinylalcohol, and wherein M is 31, N is 1, and O is 2.

Yet another object of the invention is the provision of such membrane-coated sustained-release pharmaceutical tablet exhibiting a substantially improved and superior constant dissolution rate during a major portion of its dissolution time when exposed to gastrointestinal fluid when contrasted with existing coated tablets of the art.

Still an additional object of the invention is to provide membrane-coated sustained-release pharmaceutical tablets having superior performance and sustained-release characteristics and a method of producing the same.

Another object of the invention is a provision of a membrane-coated sustained-release pharmaceutical tablet wherein the membrane exhibits excellent adhesive properties with respect to the surfaces of all types of tablets, whether said surfaces are high or low energy surfaces.

Yet a further object of the invention is to provide membrane-coated sustained-release tablets wherein the membrane coating exhibits excellent adhesive properties with respect to the tablet, whether the surface thereof is a high-energy surface or a low-energy surface, and which moreover permits superior substantially constant dissolution at a substantially constant dissolution rate during the major portion of the dissolution of the membrane-coated sustained-release pharmaceutical tablet.

Additional objects will become apparent hereinafter and still others will be obvious to one skilled in the art.

SUMMARY OF THE INVENTION

The invention may be summarized as follows:

A sustained-release coated pharmaceutical tablet comprising a drug-containing tablet and a coating or membrane surrounding the same, wherein the coating or membrane is water-insoluble and insoluble in gastrointestinal fluids and consists essentially of a terpolymer of polyvinylchloride, polyvinylacetate, and polyvinylalcohol and a water-soluble pore-creating substance, the said pore-creating substance being randomly distributed in said terpolymer coating, said pore-creating substance being present in amount of one part to 35 parts for each one to ten parts of terpolymer, said coated tablet exhibiting a substantially constant dissolution rate during a major portion of its dissolution time when exposed to gastrointestinal fluids; such coated tablet wherein the terpolymer contains 80 to 95% weight per weight of polyvinylchloride, 0.5 to 19% weight per weight of polyvinylacetate, and 0.5 to 10% weight per weight of polyvinylalcohol; such coated table wherein the pore-creating substance is a water soluble substance selected from the group consisting of saccharose, sodium chloride, and potassium chloride, or selected from the group consisting of polyvinylpyrrolidone and a polyethyleneglycol; such coated tablet wherein the pore-creating material is also solvent-soluble in solvent employed for coating of the tablet; such coated tablet wherein a plasticizer is also present in the terpolymer; such coated tabled wherein the plasticizer is present in a concentration of 0.2 to 4% weight by weight; such coated tablet wherein the plasticizer is selected from acetyltributylcitrate, polyethyleneglycol, blown castor oil, and glyceryl triacetate; such coated tablet comprising also a pH-elevating substance in the coating or membrane; such coated tablet wherein the pH-elevating substance is sodium bicarbonate; such coated tablet wherein the coating or membrane weights between 10 mg and 170 mg per tablet, depending upon the size and area of the tablet; such coated tablet wherein a second coating is present over the terpolymer coating and wherein further drug is present in the second coating; such coated tablet wherein the second coating is a rapid release coating; such coated tablet wherein the rapidrelease coating is a water-based sugar coating; such coated tablet wherein a seal coating is present between said second water-based sugar coating and the terpolymer coating; such coated tablet wherein the pore-creating substance has a particle size between about 0.5 millimicron and 50 millimicrons; such coated tablet wherein the tablet contains a drug selected from the group consisting of potassium chloride, sodium salicylate, choline theophyllinate, and paracetamole; and such coated tablet wherein the terpolymer has the approximate molecular formula (PVC)M; (PVAC)N; (PVOH)O, wherein PVC is polyvinylchloride, PVAC is polyvinylacetate, and PVOH is polyvinylalcohol, and wherein M is 31, N is 1 and O is 2. Also, a method of producing a coated tablet comprising the steps of dissolving the said terpolymer in a solvent, preparing a suspension or solution of the pore-creating substance, providing a pharmaceutical tablet, combining the suspension or solution of pore-creating substance and solvent solution of the terpolymer to form a coating fluid, applying the coating fluid in the form of a solution or suspension to the tablet, and drying the coating fluid on the tablet to provide a terpolymer-coated tablet having water-soluble pore-creating substance randomly distributed wtihin the coating or membrane; such method wherein the solvent is selected from the group consisting of acetone, methylenechloride, methylethylketone, mixtures thereof, and mixtures thereof with ethanol; such method wherein the tablet is coated with the coating fluid in the form of a solution or suspension by a coating procedure selected from the group consisting of pan coating, manual or spray coating, Würster coating, or other fluid-bed coating; such method wherein the terpolymer contains 80 to 95% weight per weight of polyvinylchloride, 0.5 to 19% weight per weight of polyvinylacetate, and 0.5 to 10% weight per weight of polyvinylalcohol; such method wherein the pore-creating substance is a water-soluble substance selected from the group consisting of saccharose, sodium chloride, and potassium chloride; or selected from the group consisting of polyvinylpyrrolidone and a polyethyleneglycol; such method wherein the pore-creating material is also solventsoluble in the solvent employed for coating of the tablet; such method wherein a plasticizer is also present in the terpolymer; such method wherein the plasticizer is present in a concentration of 0.2 to 4% weight by weight; such method wherein the plasticizer is selected from acetyltributylcitrate, polyethyleneglycol, blown castor oil, and glyceryl triacetate; such method comprising also a pH-elevating substance in the coating or membrane; such method wherein the pH-elevating substance is sodium bicarbonate; such method wherein the coating or membrane weighs between 10 mg and 170 mg per tablet, depending upon the size and area of the tablet; such method wherein a second coating is present over the terpolymer coating and wherein a further drug is present in the second coating; such method wherein the second coating is a rapid-release coating; such method wherein the said rapid-release coating is a water-based sugar coating; such method wherein a seal coating is present between said second water-based sugar coating and the terpolymer coating; such method wherein the tablet contains a drug selected from the group consisting of potassium chloride, sodium salicylate, choline theophyllinate, and paracetamole; and such method wherein the terpolymer has the approximate molecular formula (PVC)M; (PVAC)N; (PVOH)O, wherein PVC is polyvinylchloride, PVAC is polyvinylacetate, and PVOH is polyvinylalcohol, and wherein M is 31, N is 1, and O is 2.

DETAILED DESCRIPTION OF THE INVENTION

The following preparations and examples are given by way of illustration only, but are not to be construed as limiting.

The starting preparations are produced in the following manner:

(1) A terpolymer containing (w/w%) 80-95% PVC (polyvinylchloride), 0.5-19% PVAC (polyvinylacetate), and 0.5-10% PVOH (polyvinylalcohol) is dissolved in a solvent, e.g., acetone, methylenechloride, methylethylketone, or mixtures of acetone and ethanol, acetone and methylenechloride, or the like. The terpolymer is characterized by excellent adhesive properties on high-energy surfaces (Examples 1 and 5) as well as on low-energy surfaces (Example 2).

(2) A suspension or solution of the pore-creating substance is produced as follows:

The pore-creating particles are ground either by dry milling in a ball mill or by wet-milling in a glass bead milling device to a defined particle size, preferably between 0.5 μm and 50 μm. The particles are dispersed in solvents or mixtures of solvents, such as those previously mentioned, and mixed with the terpolymer solution also previously described. This mixture forms the coating fluid. Pore-creating substances are, for example, saccharose, sodium chloride, potassium chloride, or any other pharmaceutically-acceptable substance with a high degree of water-solubility. Pore-creating substances which are soluble both in water and in the previously-mentioned solvents, with or without heating, are also suitable. Examples of such pore-creating substances are PVP (polyvinylpyrrolidone) and polyethylene glycol 1500, 4000 or 6000. Terpolymers and pore-creating substances may be successfully employed in the following concentrations, weight per weight in the coating fluid:

Pore-creating substance 1-35%
Terpolymer 1-10%

Plasticizers may also be used in the coating fluid to improve the elasticity of the membrane during packaging, transport, and dissolution of the preparation. Plasticizers are generally used in concentrations between 0.2 and 4% (w/w) in the coating fluid, depending both on the coating fluid composition and the elasticity demands on the final product. Representative examples of suitable plasticizers are acetyltributylcitrate, polyethyleneglycols (1500-6000MW), blown castor oil, and glyceryl triacetate.

In order to increase the shelf-life stability of the membrane, a pH-elevating substance can also be incorporated in the membrane, e.g., sodium bicarbonate.

The coating fluid, in the form of a solution or suspension, is then applied on drug-containing cores, i.e., the tablet proper, by conventional coating procedure. Examples of such coating procedures are pan coating, manual or spray-coating, Würster coating, and other fluid-bed coating procedures.

The coating fluid has been successfully applied in such amounts that the dried membrane on each tablet weighs between 10 mg and 170 mg. The large variation in filmweight is due to the fact that tablets with different sizes and areas have been used. Furthermore, the properties of the drug, e.g., water-solubility, affect the choice of the membrane weight. Coloring matter can also be incorporated in the coating fluid, and insoluble coloring materials are preferred.

A second coating can be applied, and may contain one or more same or different drugs for which a rapid release is desirable. This coating fluid is preferably a water-based sugar coating and, therefore, a seal coating between the latter and the terpolymer membrane coating is frequently necessary or desirable.

EXAMPLES OF MEMBRANE-COATED SUSTAINED-RELEASE TABLETS ACCORDING TO THE PRESENT INVENTION.

Example 1

Membrane-Coated Potassium Chloride Tablets

Membrane coating on tablets containing potassium chloride 1 gram. Composition of the coating fluid:

|  | grams |
| --- | --- |
| Terpolymer (PVC)M (PVAC)N (PVOH)O, wherein PVC is polyvinylchloride, PVAC is polyvinylacetate, and PVOH is polyvinylalcohol, and wherein M = 31, N = 1, and O = 2 | 160 |
| Micronized powdered saccharose (particle size 1–10 μm) | 409 |
| Acetyl tributyl citrate | 35.6 |
| Blown castor oil | 26.9 |
| Sodium bicarbonate | 15 |
| Acetone ad | 4400 |

The coating process is performed in a coating pan and the coating fluid is sprayed onto the tablets with an airless spray-coating device. Five thousand tablets are coated and the average membrane weight is 60 mg per tablet.

Figure 1:
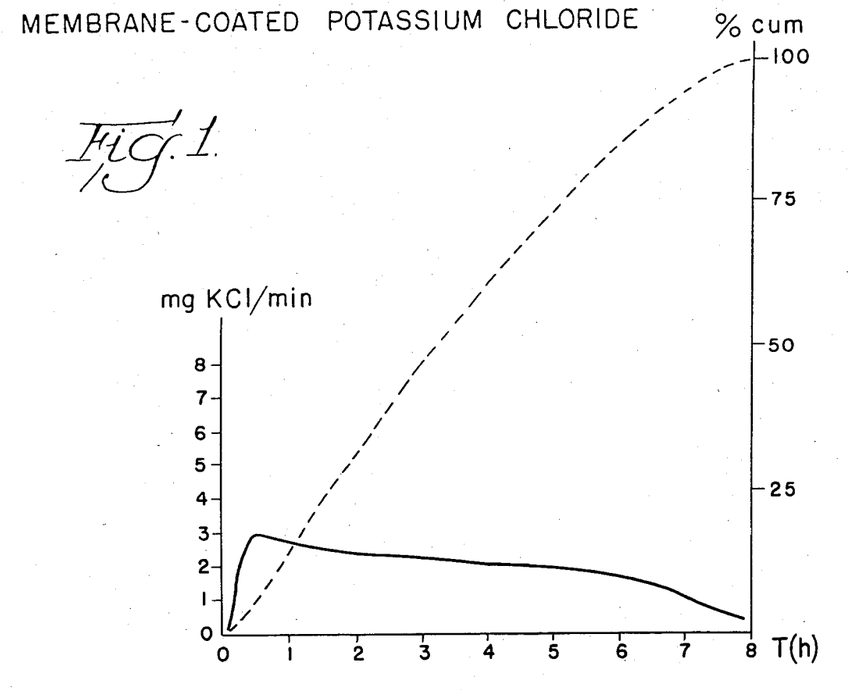
FIG. 1 is a graph showing the dissolution rate of the membrane-coated tablet of Example 1.

The dissolution rate is excellent and is shown in FIG. 1.

Example 2

Membrane-Coated Sodium Salicylate Tablets

Coating applied on tablets containing 500 mg of sodium salicylate Composition of the coating fluid:

| | grams |
|---|---|
| Terpolymer (PVC)M, (PVAC)N, (PVOH)O M = 31, N = 1, and O = 2 | 160 |
| Micronized saccharose (particle size 1–10 μm) | 409 |
| Acetyl tributyl citrate | 17.8 |
| Sodium bicarbonate | 15 |
| Acetone ad | 4400 |

The membrane weight is 50 mg per tablet and the coating procedure is the same as in Example 1.

Figure 2:
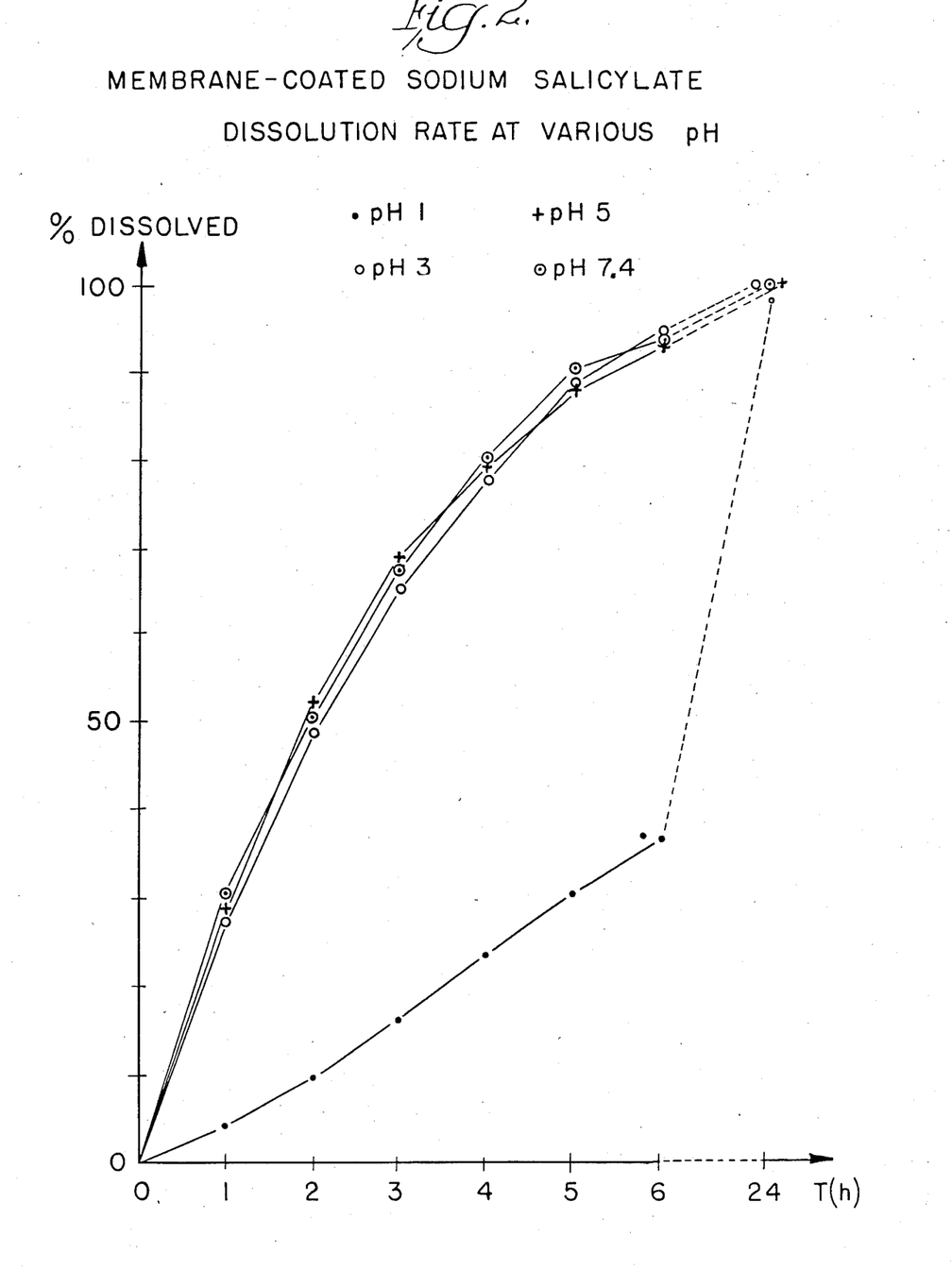
FIG. 2 is a graph showing the dissolution rate of the membrane-coated tablet of Example 2.
Figure 3:
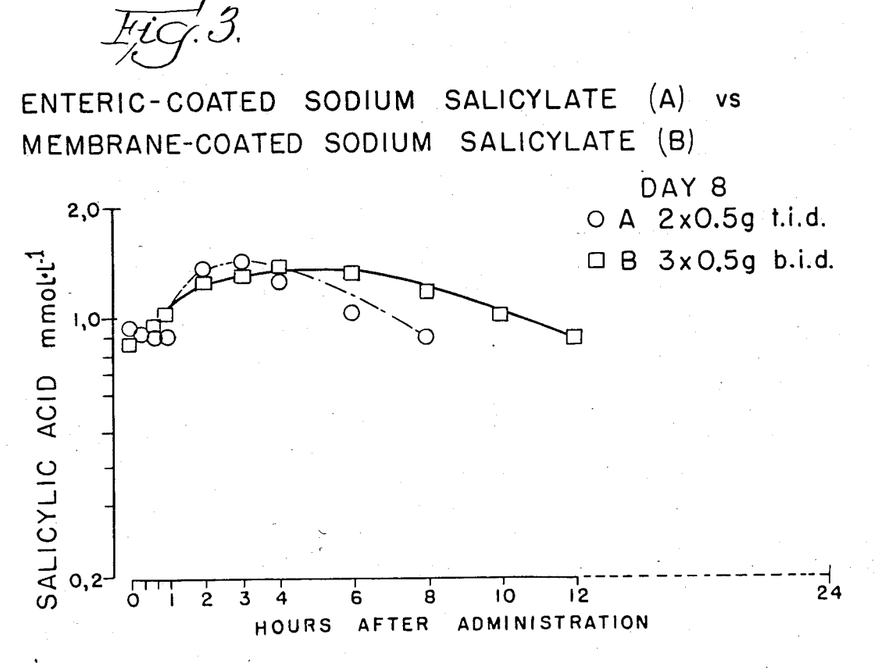
FIG. 3 is a graph showing in vivo blood-level studies of the membrane-coated tablet of Example 2 in comparison with a standard enteric-coated tablet containing the same medicament.

Dissolution rate and blood level in vivo studies are excellent and are shown in FIGS. 2 and 3.

Example 3

Membrane-Coated Choline Theophyllinate Tablets

Coating applied on tablets containing 270 mg of choline theophyllinate Composition of the coating fluid:

| | grams |
|---|---|
| Terpolymer (PVC)M, (PVAC)N, (PVOH)O M = 31, N = 1, and O = 2 | 130 |
| Micronized saccharose (particle size 1–10 μm) | 409 |
| Acetyltributyl citrate | 14.3 |
| Blown castor oil | 10.9 |
| Sodium bicarbonate | 15 |
| Acetone ad | 4400 |

The weight of the membrane is 40 mg per tablet and the coating procedure is the same as in Example 1.

Figure 4:
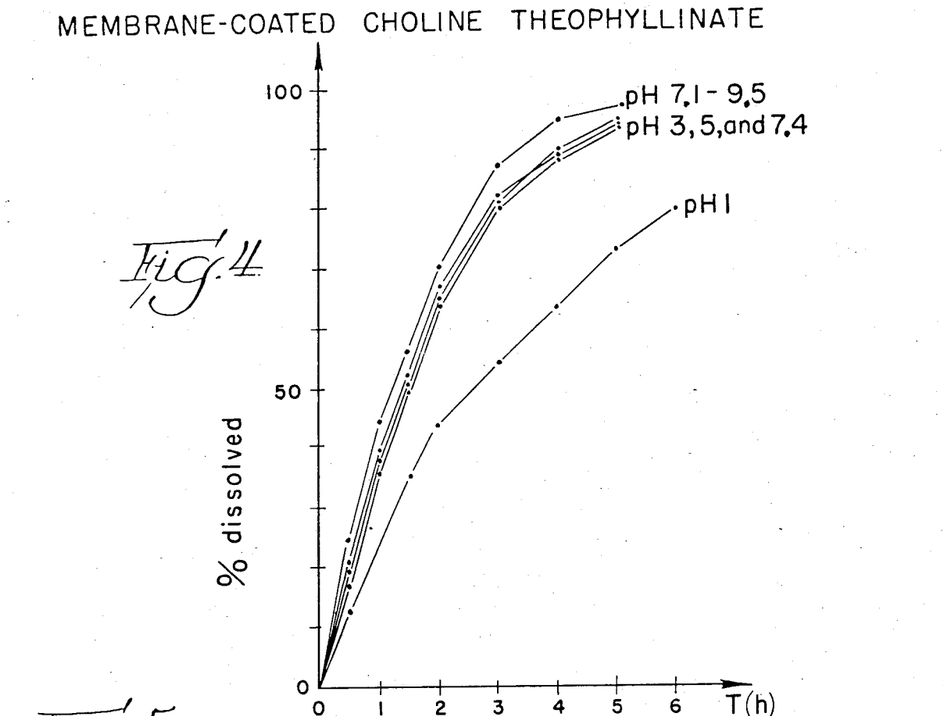
FIG. 4 is a graph showing the dissolution rate of the membrane-coated tablet of Example 3 at varying pHs.
Figure 5:
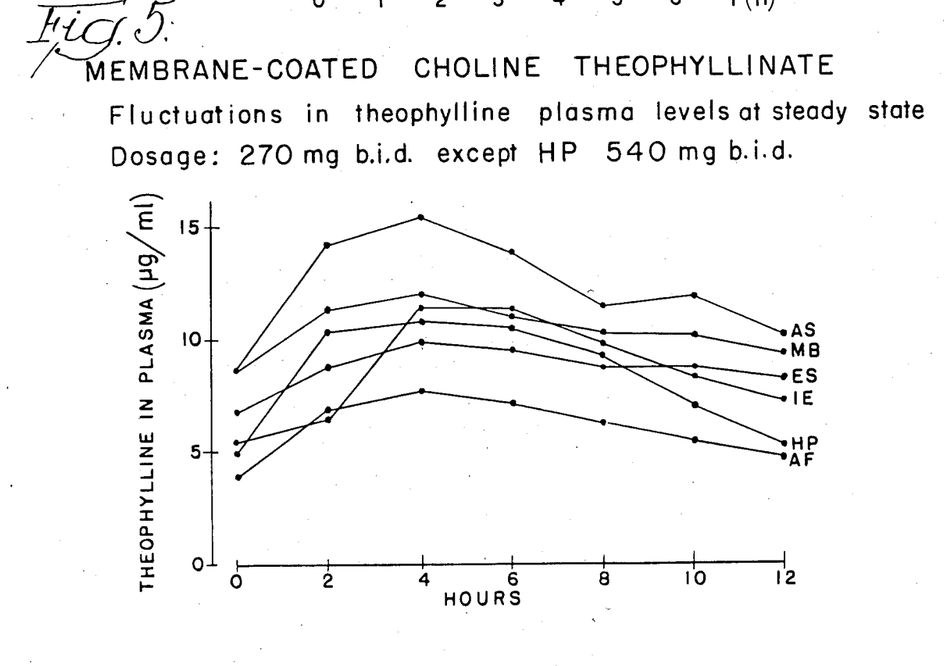
FIG. 5 is a graph showing in vivo blood-level studies of the membrane-coated tablet of Example 3 in various adult subjects.

Dissolution rate and results of in vivo experiments are excellent and are shown in FIGS. 4 and 5.

Example 4

Membrane-Coated Paracetamole Tablets

Coating applied on tablets containing 500 mg of paraacetaminophenol
Composition of the coating fluid:

| | grams |
|---|---|
| Terpolymer (PVC)M, (PVAC)N, (PVOH)O M = 31, N = 1, and O = 2 | 120 |
| Polyethyleneglycol 6000 (pore-creating substance) | 410 |
| Acetyl tributyl citrate | 12 |
| Acetone ad | 4400 |

The coating procedure is the same as in Example 1.

The coating solution is applied at a temperature of 43° C. and the weight of the dry membrane on each tablet is 17 mg.

Figure 6:
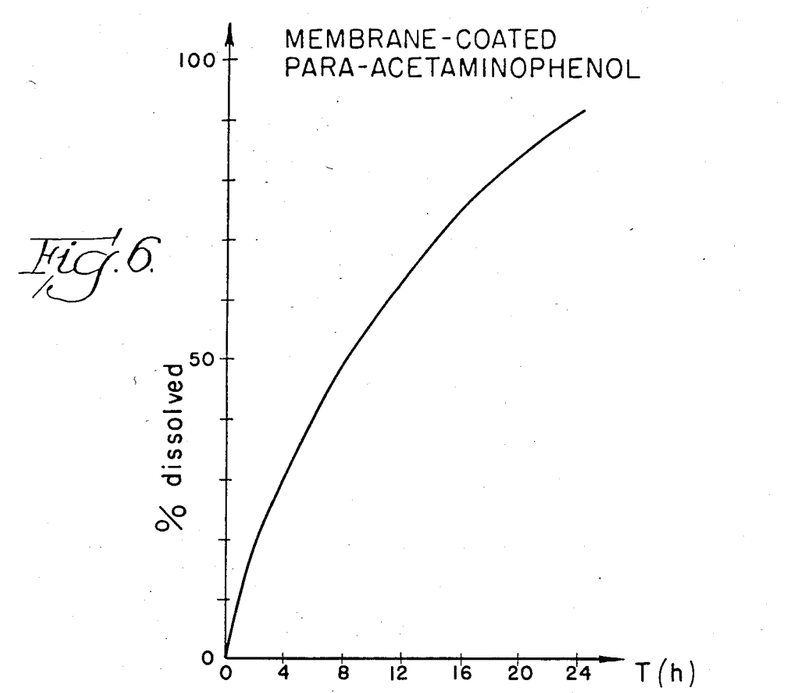
FIG. 6 is a graph showing the dissolution rate of the membrane-coated tablet of Example 4.

Dissolution rate is excellent and is shown in FIG. 6.

Example 5

Terpolymer Variation

Coating applied on tablets containing 1 g of potassium chloride
Composition of the coating fluid:

| | grams |
|---|---|
| Terpolymer (PVC)M, (PVAC)N, (PVOH)O M = 100, N = 1, and O = 8 | 160 |
| Micronized powdered saccharose (particle size 1–10 μm) | 409 |
| Acetyltributyl citrate | 35.6 |
| Blown castor oil | 26.4 |
| Sodium bicarbonate | 15 |

-continued

| | grams |
|---|---|
| Acetone ad | 4400 |

The weight of the dried membrane was 60 mg per tablet and the coating procedure was the same as in Example 1.

Figure 7:
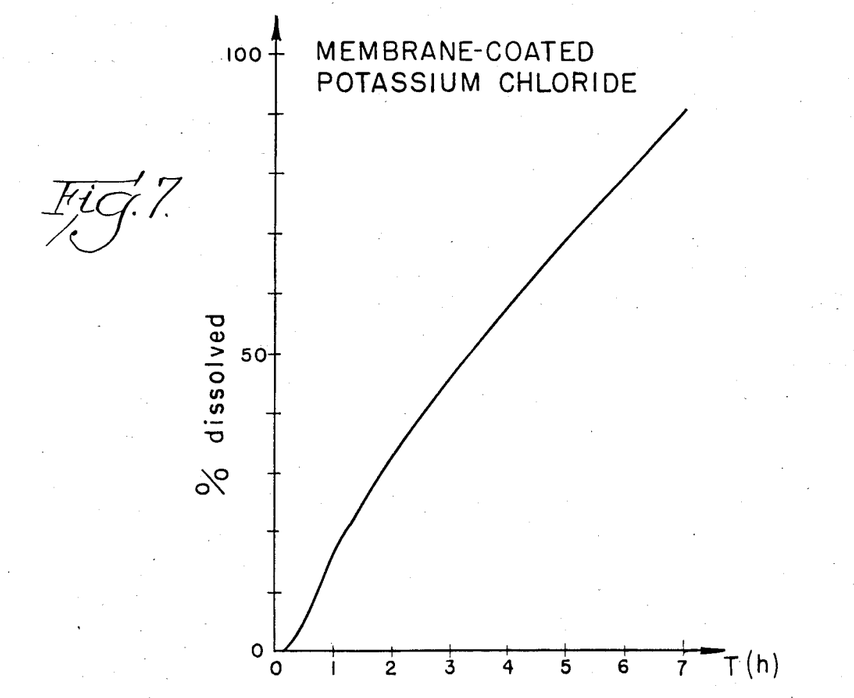
FIG. 7 is a graph showing the dissolution rate of the membrane-coated tablet of Example 5.

Dissolution rate is excellent and is given in FIG. 7.

Example 6

Additional Variations

In addition to the foregoing specific exemplifications of the present invention, numerous variations in the type of drug and the type of tablet may be employed in accord with the general disclosure of this application, as well as further variations in the terpolymer coating, especially within the preferred ranges of 80 to 95% weight per weight of polyvinylchloride, 0.5 to 19% weight per weight of polyvinylacetate, and 0.5 to 10% weight per weight of polyvinylalcohol, without departing from the scope of the invention or the essential advantages, namely, substantially constant dissolution rate during the major portion of the dissolution when exposed to gastrointestinal fluids and the prolonged and predictable blood levels resulting therefrom, all as evidenced by the foregoing Examples and the dissolution time and the rate graphs and blood level graphs set forth in the FIGS. relating thereto, as well as tenacious adhesion or adherence of the membrane coating to all types of tablet surfaces, whether low or high energy surfaces.

IN GENERAL

The present invention relates to a way of manufacturing medicinal preparations with controlled release of the drug and to the product produced thereby. The invention relates to tablets constituting individual units, which are covered with a coating containing a specific type of polymer and a pore-creating substance. A preparation manufactured according to this principle of "membrane coating" and according to the invention exhibits an almost constant dissolution rate during a major part of the dissolution time.

When the coating or membrane, consisting essentially of the water-insoluble polymer and a water-soluble pore-creating substance, is exposed to gastrointestinal fluids, the pore-creating substance is dissolved and pores are generated. During manufacture, the pore-creating particles or droplets are randomly distributed over the tablet surface and in the polymer layer. The dissolution medium then penetrates through the pores into the core or tablet proper and dissolves the drug contained therein. The close to saturated solution which forms inside the membrane then diffuses out through the pores. The diffusion rate depends on a number of factors such as the number of pores, pore size, the solubility of the drug in the actual dissolution medium, and so on. These parameters can readily be controlled and they can also be varied within broad limits. The diffusion through the membrane is governed by the concentration gradient between the inside and outside of the membrane and, as long as any drug in solid form is present inside the membrane, the interior drug concentration will be fairly constant. The drug concentration outside the membrane is very small due to the large volume of dissolution medium and the fact that the drug is continuously absorbed by the system of the subject to which administered. Noyes-Whithey's equation can be applied and is representative of this principle.

It is as follows:

$$dC/dt = K \cdot S (C_s - C)$$

where
$C_s$ = Concentration inside the membrane
$C$ = Concentration outside the membrane
$K$ = Diffusion constant
$S$ = Area of the membrane
$dC/dt$ = Diffusion rate
$C$, the concentration outside the membrane, can here be neglected and the following equation remains:

$$dC/dt = K \cdot S \cdot C_s$$

The diffusion constant K and the area S are also constants and, therefore, the diffusion rate will be directly proportional to $C_s$. As earlier emphasized, the concentration inside the membrane $C_s$ will be relatively constant inasmuch as any solid drug remains inside the membrane. In FIG. 1 the dissolution rate of a membrane-coated potassium chloride tablet is presented. The dissolution rate is determined by the ascending column method. After six hours, the dissolution rate decreases rapidly due to the fact that no solid drug remains within the membrane. The dissolution rate then follows first order kinetics.

THE DRUG

The present invention is not limited in either its membrane-coated sustained-release tablet aspect or in its method aspect by the drug or type of drug incorporated in the tablet. Innumerable orally-acting drugs are known, marketed commercially, and set forth in the prior art, and any tablet containing any presently known or future-discovered orally-acting drug may be coated according to the present invention to provide the highly advantageous constant-dissociating pharmaceutical tablets of the present invention. Numerous drug-containing tablets, wherein the type of drug or medicament is varied, are set forth in the Examples hereof, but other drugs without limitation may be employed. A suitable definition and revelation of other orally-acting drugs and types of drugs may be found by reference to the latest US Pharmacopia or to Remington on Pharmacy or to the specifications and examples of U.S. Pat. Nos. 1,907,203, 2,196,768, 2,433,244, 2,753,288, 2,875,130, and 2,881,113 for tablet forms which may be coated and placed into the form of membrane-coated sustained-release pharmaceutical tablets according to the present invention. Reference is also made to U.S. Pat. No. 3,143,463, columns 3 and 4, for types of tablets, tableting diluents and adjuvants, as well as usual types of formulations and percentages of ingredients, although the tableting art is so well established that anyone skilled in the art today knows without further instructions how to place any particular drug or medicament into tablet form and any such tablet may be membrane-coated and turned into a membrane-coated sustained-release pharmaceutical tablet according to the present invention simply by following the instructions of the present application. Further types of drugs which may be employed are fully set forth in columns 10 and 11 of U.S. Pat. No. 4,144,317, issued Mar. 13, 1979, and reference to this patent is hereby made for various types of drugs which may be incorporated into tablets which may then be converted into membrane-coated sustained-release pharmaceutical tablets according to the present invention, and the disclosure of the said U.S. Pat. No. 4,144,317 is herein incorporated by reference to the extent necessary or desirable for purposes of illustrating the multitude of drugs and type of drugs which are already known to be incorporatable into tablets and then membrane-coated to provide a membrane-coated sustained-release pharmaceutical tablet according to the present invention.

PHARMACOLOGY

Representative membrane-coated sustained-release tablets of the present invention have been subjected to a series of in vitro and in vivo tests in which the new products have been shown to have a substantially constant and long-acting dissolution rate during a major portion of their dissolution time when exposed to gastrointestinal fluids and, in many cases, to have extremely valuable and superior characteristics when compared with control substances, for example, the usual enteric-coated product compared with in FIG. 3.

The methods of determining blood levels employed for the membrane-coated sustained-release pharmaceutical tablets of the present invention are as follows:

1. Bates, Bernstein, "A Rapid Microcapillary Determination of Serum Theophylline", presented at the 28th national meeting of the American Association of Clinical Chemists, Aug. 1–6, 1976, Houston, Tex., USA.

2. Blood levels of sodium salicylate—these determinations were made at Malmö General Hospital, Malmö, Sweden, by an entirely routine method which is well known in the art.

Publications regarding the dissolution rate of drug contained in the membrane-coated sustained-release tablet of the invention, the procedure of which was employed and reported herein, are as follows:

1. F. Langenbucher, "Flow Cell Determinations", J. Pharm. Sci.,58, 1165 (1969).

2. John W. Poole, "Beaker Determinations", Drug Information Bulletin 3 (1969).

It is to be understood that the invention is not to be limited to the exact details of operation or to the exact compounds, compositions, methods, procedures, or embodiments shown and described, as numerous modifications and equivalents will be apparent to one skilled in the art and may be made without departing from the spirit or scope of the invention, which is therefore to be limited only by the full scope of the appended claims.

We claim:

1. Method of administering a drug for sustained-release purposes comprising the step of orally administering the drug in the form of a sustained-release coated pharmaceutical tablet thereof comprising the drug-containing tablet and a coating or membrane surrounding the same, wherein the coating or membrane is water-insoluble and insoluble in gastrointestinal fluids and consists essentially of a terpolymer of polyvinylchloride, polyvinylacetate, and polyvinylalcohol and a water-soluble pore-creating substance, the said pore-creating substance being randomly distributed in said terpolymer coating, said pore-creating substance being present in amount of one part to 35 parts for each one to ten parts of terpolymer, said coated tablet exhibiting a substantially constant dissolution rate during a major portion of its dissolution time when exposed to gastrointestinal fluids, wherein the terpolymer contains about 80 to 95% weight per weight of polyvinylchloride, 0.5 to 19% weight per weight of polyvinylacetate, and 0.5 to 10% weight per weight of polyvinylalcohol.

2. Method of claim 1, wherein the pore-creating substance is a water-soluble substance selected from the group consisting of saccharose, sodium chloride, and potassium chloride.

3. Method of claim 1, wherein the pore-creating substance is a water-soluble material selected from the group consisting of polyvinylpyrrolidone and a polyethyleneglycol.

4. Method of claim 1, wherein the porecreating material is also solvent-soluble in solvent employed for coating of the tablet.

5. Method of claim 1, wherein a plasticizer is also present in the terpolymer.

6. Method of claim 5, wherein the plasticizer is present in a concentration of 0.2 to 4% weight by weight.

7. Method of claim 6, wherein the plasticizer is selected from acetyltributylcitrate, polyethyleneglycol, blown castor oil, and glyceryl triacetate.

8. Method of claim 5, comprising also a pHelevating substance in the coating or membrane.

9. Method of claim 8, wherein the pH-elevating substance is sodium bicarbonate.

10. Method of claim 1, wherein the coating or membrane weighs between 10 mg and 170 mg per tablet, depending upon the size and area of the tablet.

11. Method of claim 10, wherein a second coating is present over the terpolymer coating and wherein further drug is present in the second coating.

12. Method of claim 11, wherein the second coating is a rapid-release coating.

13. Method of claim 12, wherein the said rapid-release coating is a water-based sugar coating.

14. Method of claim 13, wherein a seal coating is present between said second water-based sugar coating and the terpolymer coating.

15. Method of claim 1, wherein the porecreating substance has a particle size between about 0.5 millimicron and 50 millimicrons.

16. Method of claim 15, wherein the tablet contains a drug selected from the group consisting of potassium chloride, sodium salicylate, choline theophyllinate, and paracetamole.

17. The coated tablet of claim 1, wherein the terpolymer has the approximate molecular formula (PVC)M; (PVAC)N; (PVOH)O; wherein PVC is polyvinylchloride, PVAC is polyvinylacetate, and PVOH is polyvinylalcohol, and wherein M is 31, N is 1 and O is 2.

* * * * *

UNITED STATES PATENT AND TRADEMARK OFFICE
CERTIFICATE OF CORRECTION

PATENT NO. : 4,629,620

DATED : December 16, 1986

INVENTOR(S) : Ake R. Lindahl and Stig A. B. Erlandsson

It is certified that error appears in the above-identified patent and that said Letters Patent is hereby corrected as shown below:

Col. 3, line 67; "weights" should read -- weighs --

Col. 4, line 47; "solventsoluble" should read -- solvent-soluble --

Col. 6, last line; "Composition of the coating fluid:" should be a new paragraph.

Col. 7, line 19; "Composition of the coating fluid:" should be a new paragraph.

Col. 11, line 12; "porecreating" should read -- pore-creating --

Col. 11, line 23; "pHelevating" should read -- pH-elevating --

Col. 12, line 14; "porecreating" should read -- pore-creating --

Col. 12, line 21; "The coated tablet" should read -- Method --

Signed and Sealed this

Sixth Day of June, 1989

*Attest:*

DONALD J. QUIGG

*Attesting Officer*

*Commissioner of Patents and Trademarks*